United States Patent [19]

Sasaki et al.

[11] Patent Number: 5,531,775
[45] Date of Patent: Jul. 2, 1996

[54] SKIN ATTACHMENT TYPE ELECTRIC THERMAL TREATMENT DEVICE

[75] Inventors: Minoru Sasaki, Yokohama; Sinichirou Watanabe, Tokyo, both of Japan

[73] Assignee: Kabushiki Kaisya Advance, Tokyo, Japan

[21] Appl. No.: 266,877

[22] Filed: Jul. 5, 1994

Related U.S. Application Data

[63] Continuation of Ser. No. 3,486, Jan. 12, 1993, abandoned.

[30] Foreign Application Priority Data

Jul. 19, 1991 [JP] Japan ................... 3-84712 U

[51] Int. Cl.$^6$ ..................................... A61F 7/00
[52] U.S. Cl. ......................................... 607/96
[58] Field of Search ............... 219/211; 607/96, 607/98, 99, 102, 101, 115

[56] References Cited

U.S. PATENT DOCUMENTS

| | | | |
|---|---|---|---|
| 4,273,989 | 6/1981 | Hinton | 219/211 |
| 4,279,255 | 7/1981 | Hoffman | 128/399 |
| 4,653,491 | 3/1987 | Okada et al. | 128/138 |
| 4,860,748 | 8/1989 | Chiarco et al. | 607/112 |

FOREIGN PATENT DOCUMENTS

| | | |
|---|---|---|
| 2931610 | 2/1981 | Germany . |
| 59-36339 | 3/1984 | Japan . |
| WO86/07662 | 12/1986 | WIPO . |

*Primary Examiner*—Mark S. Graham
*Attorney, Agent, or Firm*—Finnegan, Henderson, Farabow, Garrett and Dunner

[57] ABSTRACT

The present invention provides an electric thermal treatment device that uses no battery, has a compact design, enables satisfactory thermotherapy, and completes charging quickly. The electric thermal treatment device comprises a heating unit including a charge storage, a heater that generates heat using current discharged from the charge storage, and an attachment that attaches the device to the skin, and a power supply unit for supplying a charge to the charge storage in the heating unit. The heating unit is electrically coupled with the power supply unit to receive charge. After being decoupled from the power supply unit, the heating unit is attached to the skin of human body and generates heat.

4 Claims, 4 Drawing Sheets

SKIN ATTACHMENT TYPE ELECTRIC THERMAL TREATMENT DEVICE

This application is a continuation, of application Ser. No. 08/003,486, filed Jan. 12, 1993, now abandoned.

BACKGROUND OF THE INVENTION

1. Field of the Invention

The present invention relates to an electric thermal treatment device that is attached to the skin for use.

2. Description of the Related Art

Thermal treatment in the present invention includes moxibustion. An electric thermal treatment device which is attached to the skin for use must use a button or coin type small-capacity battery.

To apply heat of abut 70° C. to a living body, a battery must supply a large current to a heating element.

However, to satisfy the above requirement, a large battery must be used.

On the other hand, a mode in which a secondary battery is used alternately as a primary battery has been proposed. This mode requires a long charging time. When charging is completed quickly, overcharge is likely to occur. As a result, gas is generated in the battery. This deteriorates the battery.

SUMMARY OF THE INVENTION

Accordingly, a debut of a skin attachment type electric thermal treatment device that is safe in use, requires a short time for charging a battery, and has a long service life has been awaited.

To achieve the above object, the present invention adopts the art and construction mentioned below.

To be more specific, a skin attachment type electric thermal treatment device comprises a heating unit including a charge storage means, a heating means that generates heat using current discharged from the charge storage means, and an attaching means for attaching the device to the skin, and a power supply unit for supplying a charge to the charge storage means in the heating unit. The heating unit is electrically coupled with the power supply to receive a charge. After separated from the power supply unit, the heating unit is attached to the skin of a human body and generates heat.

DESCRIPTION OF THE PREFERRED EMBODIMENTS

An embodiment of a skin attachment type electric thermal treatment device according to the present invention will be described in detail with reference to the drawings.

Figure 1:
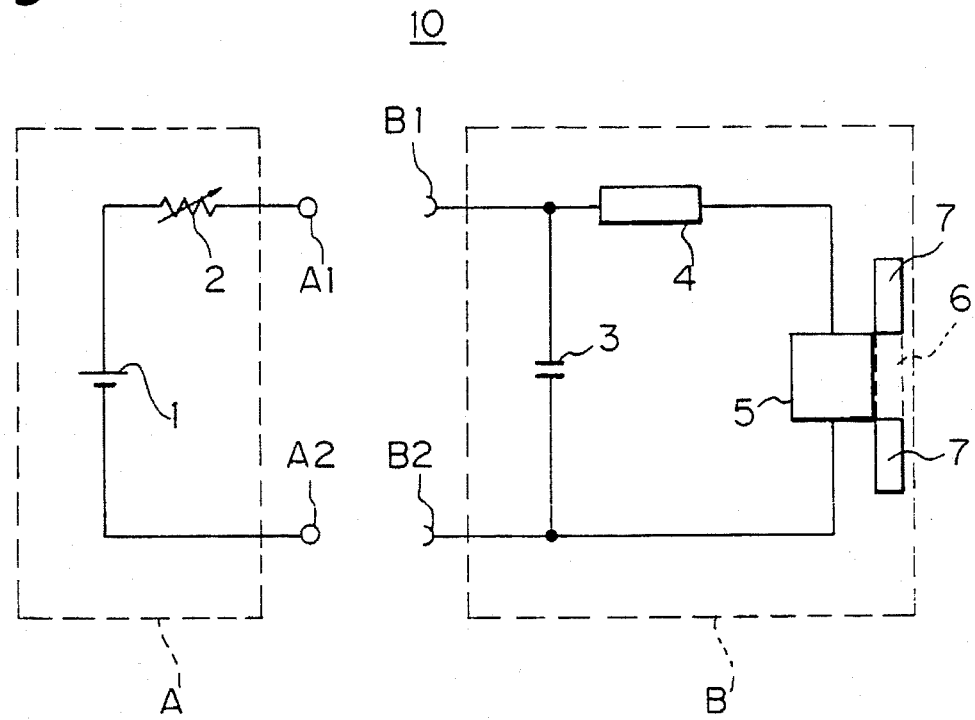
FIG. 1 is a block diagram of an embodiment of the present invention.

FIG. 1 is a block diagram showing a construction of an embodiment of a skin attachment type electric thermal treatment device according to the present invention. The skin attachment type electric thermal treatment device comprises a heating unit B including a charge storage means 3, a heating means 5 that generates heat using current discharged from the charge storage means 3, and an attaching means that attaches the device to the skin, and a power supply unit A for supplying charge to the charge storage means in the heater B. The heating unit B is electrically coupled with the power supply unit A to receive a charge. After being decoupled from the power supply unit A, the heating unit B is attached to human skin and generates heat.

In the present invention, a charge storage means is employed instead of a battery. Thereby, a compact thermal treatment device which involves no risk and permits a short charging time has been realized.

The charge storage means 3 in the present invention is, for example, a capacitor. A super capacitor having a capacitance of about 1 farad is employed. A button-type super capacitor, which is about 20 mm in diameter and about 5 mm in thickness, compact and lightweight, and has a capacitance of 1 farad or more, has been placed on the market. This kind of capacitor is preferable for the present invention. The capacitance, size, and shape are selected according to the purpose of use. The present invention may include a plurality of charge storage means which are to be operated simultaneously or sequentially.

An embodiment of the present invention will now be described in more detail. A denotes a power supply unit, and B denotes a heating unit. In the power supply unit A, 1 denotes an electric energy supplying means. The electric energy supplying means is made up of primary and secondary batteries, or realized with a DC power supply for rectifying and smoothing mains AC power or a switching power supply. Reference 2 denotes an adjusting means. The adjusting means 2 is a device or circuit for adjusting a voltage and current; such as, a variable resistor, an on/off switch, or a boosting circuit. Reference A1 and A2 denote output terminals. In the heating unit B, 3 denotes a charge storage means that is a capacitor. Reference 4 denotes a control means that is, for example, an on/off switch, variable resistor, or switching control circuit. Reference 5 denotes a heating element (heating means). The heating element 5 is a ceramic body around which a platinum, Nichrome, or tungsten wire is wound, a filament made of a Nichrome wire, a tungsten wire, platinum, gold, or silver, or a ceramic on which tungsten or silver and palladium is printed or deposited. References B1 and B2 denotes input terminals. Reference 6 denotes a buffering member, which is paper, moxa, or a space. The buffering member 6 is not indispensable to the present invention but is employed depending on a heating value of a heating element. Therefore, the heating element may directly be in contact with a living body. In this case, it is preferred that the ceramic of the heating element 5 is brought into contact with the living body. Reference 7 denotes an attaching member that attaches the treatment device to human skin and is an adhesive.

The connections of the aforesaid components will now be described.

One terminal of an electric energy supplying means 1 in a heating unit A is connected to one terminal of an adjusting means 2. The other terminal of the adjusting means 2 is connected to an output terminal A1. The other terminal of the electric energy supplying means 1 is connected to an output terminal A2. One terminal of a charge storage means 3 is connected to an input terminal B1 and to one terminal of a control means 4. The other terminal of the control means 4 is connected to one terminal of a heating element 5. The other terminal of the heating element 5 is connected to the other terminal of the charge storage means 3 and to an input terminal B2. When the output terminals A1 and A2, and the input terminals B1 and B2 are coupled mechanically, the output terminals A1 and A2, and the input terminals B1 and B2 are coupled electrically. It is possible to decouple the output terminals A1 and A2, and the input terminals B1 and B2.

Next, the operation will be described with reference to FIG. 2.

Figure 2A:
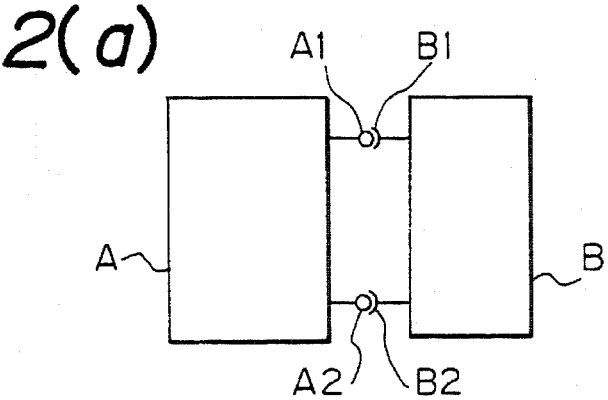
FIGS. 2(a) and 2(b) are explanatory diagrams for the operation of the embodiment shown in FIG. 1.
Figure 2B:
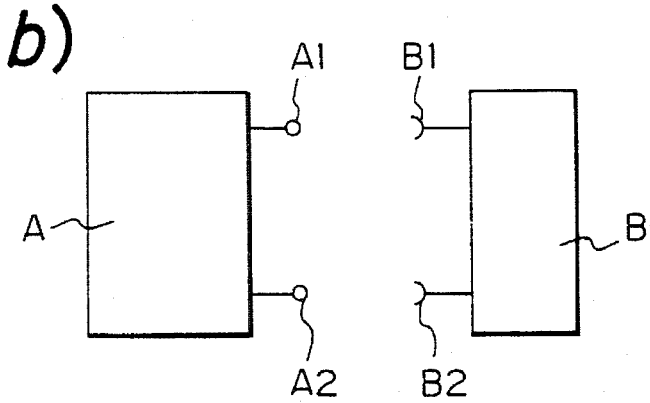

During charging, as shown in FIG. 2, an output terminal A1 and an input terminal B1, and an output terminal A2 and an input terminal B2 are respectively connected to each other. Electric energy from an electric energy supplying means 1 is attenuated or boosted using an adjusting means 2, and is then fed to a charge storage means 3 in a heating unit B. A control means 4 electrically disconnects a heating element 5 and the charge storage means 3. The charge storage means 3 stores electric energy. After a given amount of electric energy has been stored or after a given time has elapsed, as shown in FIG. 2b, the connections between the output terminals A1 and A2, and the input terminals B1 and B2 are released to decouple the power supply unit A and the heating unit B.

The heating element 5 in the heating unit B is applied to a lesion of a living body. A buffering member 6 made of paper, for example, is placed between the heating element 5 and the lesion of the living body. The buffering member 6 is not limited to paper but may be moxa or a space. The buffering member 6 buffers and retains heat generated by the heating element 5.

The control means 4 in the heating unit B is activated to supply a charge stored in the charge storage means 3 to the heating element 5. The heating element 5 receives the charge to generate heat. The heat of the heating element 5 is supplied to the lesion of the living body via the buffering member 6. The buffering member 6 buffers heat of the heating element 5 to provide the living body with a comfortable warm feeling. Even after the heating element stops generating heat, since the buffering member 6 retains heat, the living body will still have the satisfactory warm feeling.

The control means 4 controls a charge (electric energy) to be supplied to the heating element. The control mode is diverse. For example, the control means 4 is made up of a microcomputer and a relay that is turned on or off with a drive pulse provided by the microcomputer. Alternatively, the control means 4 is realized with a FET or other switching device. The switching device electrically couples a charge storage means and a heating device. When the switching device repeats on/off switching, a charge supplied to the heating device becomes intermittent. Thus, the temperature of the heating device is controlled.

In a variant, the control mens 4 is a manual on/off switch. The control means 4 may be made up of a thermostat and a manual on/off switch.

In another variant, the control means 4 is a switching means that disconnects a charge storage means and a heating element when a power supply unit A and a heating unit B are connected, and that connects the charge storage means and the heating element when the power supply unit A and heating unit B are disconnected.

The control means is not limited to the aforesaid examples but may be made up of a resistor, a timer, and a switching device. Therefore, the control means may assume any form as long as it can control electrical coupling between a charge storage means and a heating element so that the heating element can generate sufficient heat for at least thermotherapy. The control means may operate in a mode in which a thermal treatment is carried out several times by supplying charge from the charge storage means to the heating element little by little several times.

When a microcomputer is employed for the control means, power for the microcomputer is preferably supplied from the charge storage means. Alternatively, a button battery may be added as the power supply for the microcomputer.

Figure 3:
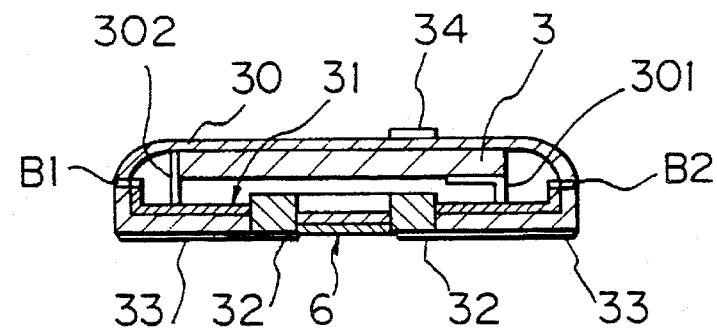
FIGS. 3, 4, and 6 show an embodiment of the present invention.
Figure 4:
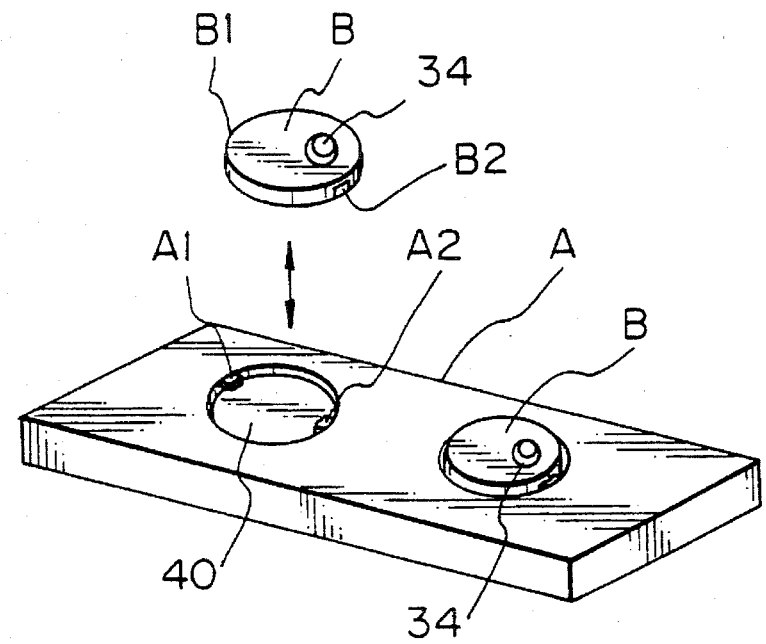

FIG. 3 shows an example of a construction of a heating element, and FIG. 4 shows an example of an appearance of a heating unit and a power supply unit.

In FIG. 3, 30 denotes a main body case that is made of a hard plastic and shaped like a disk. 34 denotes a switch. The switch 34 is mounted on the main body case 30 and connected to a control means 4 shown in FIG. 1.

The switch 34 is of the push type. When pressed, the switch 34 is turned on to couple a charge storage means 3 and a heating element 5 shown in FIG. 1. When pressed again, the switch 34 is turned off to decouple the charge storage means 3 and heating element 5. The switch 34 may be of the sliding type. The role of the switch 34 varies depending on the control mode of the control means 4. For example, the control means 4 may have such a function that increments or decrements a heating value of the heating element 5 with every push of the switch 34.

Reference 31 denotes an electronic substrate. The charge storage means 3 and control means 4 of a heating unit B shown in FIG. 1 are mounted on the electronic substrate 31.

Reference 32 denotes a heat retaining member. The heat retaining member 32 has a hollow in which the heating element 5 is held. It is preferred that the sides of the heat retaining member 32 are made of a heat insulating material. The heat insulating material is not limited to any specific one but may be Bakelite, a heat insulating plastic, paper, or ceramic. Reference 6 denotes a buffering member, which may be paper or a space.

Reference 3 denotes a charge storage means, which is connected to the substrate 31 using current-carrying pins 301 and 302.

On the sides of the main body case 30, input terminals B1 and B2 are arranged to extend outside. On the bottom of the main body case 30, the heating element 5 is exposed and surrounded with an adhesive layer (attaching means) 33. The composition of the adhesive layer 33 is not limited to any specific one as long as it is irresponsive to a living body.

An adhesive layer is formed on the bottom of the heating element 1. Alternatively, a heating element that is not adhesive and an adhesive tape may be used in combination.

FIG. 4 is an oblique view of an example of a power supply unit A and a heating unit B shown in FIG. 3. In the power supply unit A, a recess 40 for accommodating the heating unit B is formed. Output terminals A1 and A2 are exposed from the sides of the recess 40. When the heating unit B is accommodated in the recess 40 of the power supply unit A, the input terminal B1 formed on the side of the heating unit B is brought into contact with the output terminal A1 of the power supply unit A, and the input terminal B2 of the heating unit B is brought into contact with the output terminal A2 of the power supply unit A. Thus, preparations for charging the heating unit B are completed.

The charging time varies depending on the charge storage means incorporated in the heating unit B or on the capacity of the charge storage means.

Figure 5:
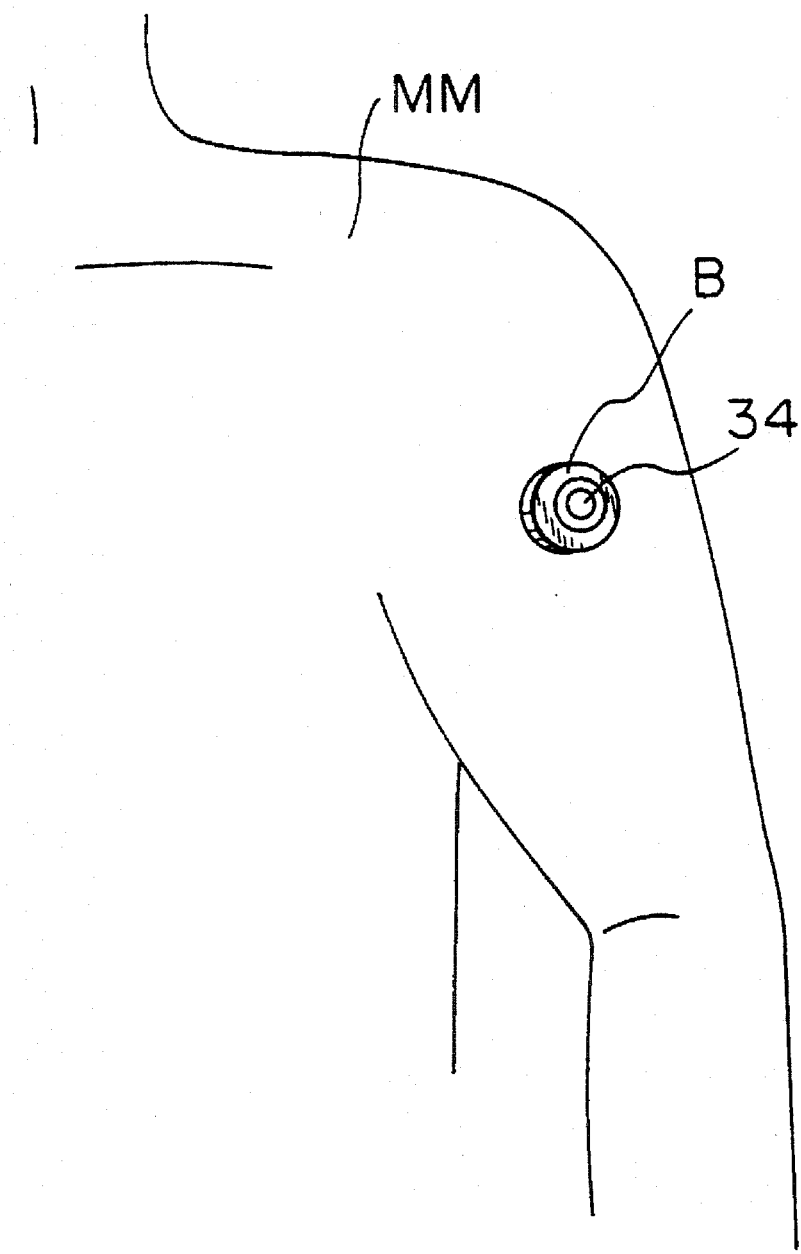
FIG. 5 is an explanatory diagram showing a state of use of an embodiment of the present invention.

After charging is completed, the heating unit B is picked up from the power supply unit A. Then, the adhesive layer 33 of the heating unit B is applied to a lesion of a living body. With the adhesion of the adhesive layer 33, the heating unit B is attached to the lesion of the living body. FIG. 5 shows the state of application. MM denotes a human body. The brachium and its peripheral regions are shown schematically. Reference B is the heating unit. When the switch 34 is pressed, the heating element 5 arranged on the bottom of the heating unit B and shown in FIG. 3 starts generating heat. Heat generated by the heating element 5 is buffered by the buffering member 6, then transmitted to the lesion of the living body. Thus, a thermal treatment starts. After that, heat generation is performed once or repeatedly under the control of the control means 4.

Figure 6:
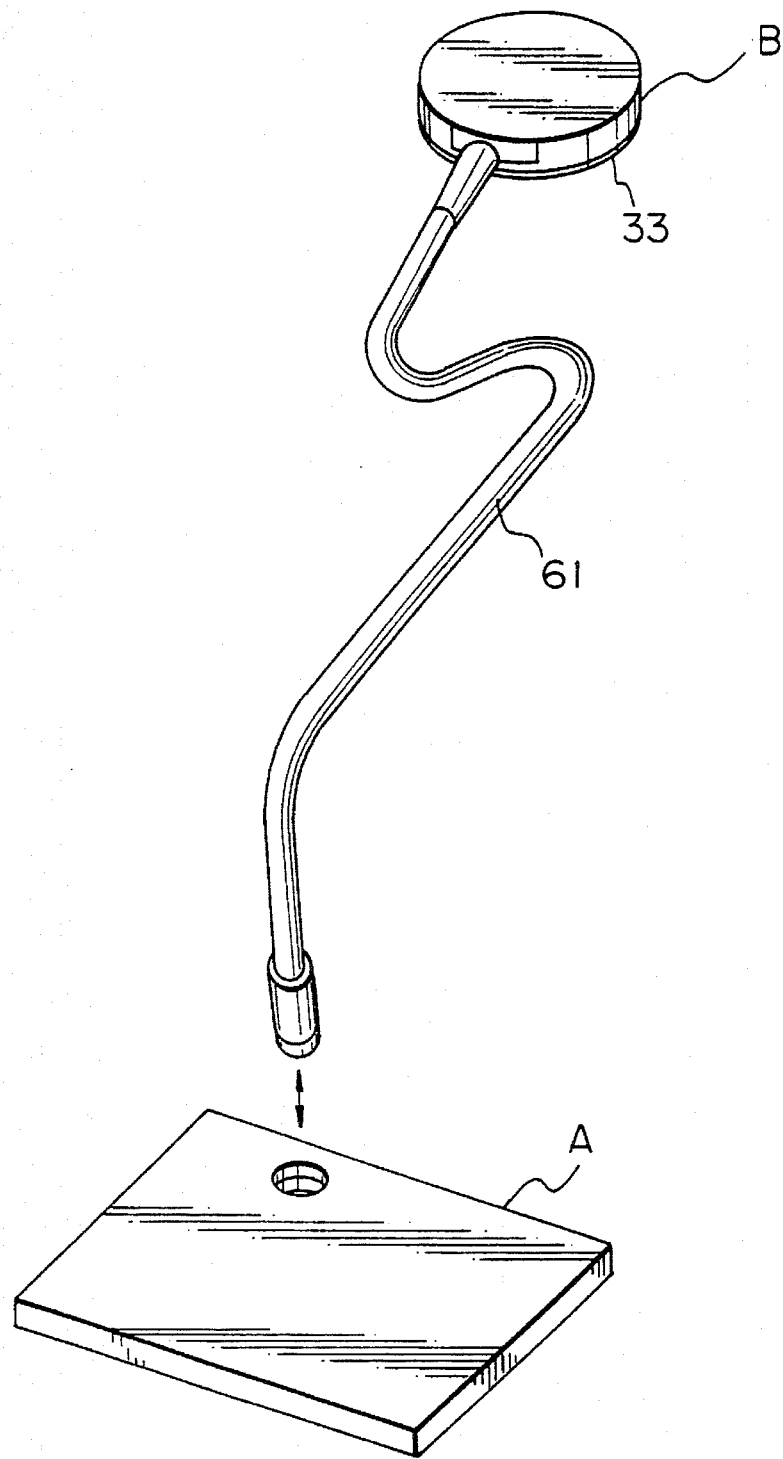

The present invention permits a mode in which the power supply unit A and heating unit B are connected using a charging cord and a terminal 61 as shown in FIG. 6. The charging cord and terminal 61 are removed when the heating unit B is attached to a lesion of a living body.

However, the charging cord and terminal 61 may not be removed but may remain connected even after the heating unit B is attached to a lesion of a living body and heat generation starts.

The present invention has the advantages that since a charge storage means is used as a source of supplying electric energy, no content oozes out due to deterioration caused by the use of a battery, a treatment procedure is safe, and charging is completed more quickly than charging a battery.

We claim:

1. A skin attachment type electric thermal treatment device, comprising:

a heating unit including a capacitor charge storage means, a heating means that generates heat using current discharged from said capacitor, and an attaching means for attaching the device to the skin; and a power supply unit for supplying charge to said capacitor of said heating unit;

said heating unit being electrically coupled with said power supply unit to receive a charge, then attached to the skin of a human body after decoupled from said power supply unit; and a control means comprising a switching device and a microcomputer, said control means controlling the temperature of said heating means by intermittently supplying current to said heating means.

2. A skin attachment type electric thermal treatment device according to claim 1, wherein said heating unit and said power supply unit are independent of each other, and are freely coupled with and decoupled from each other.

3. The skin attachment type electric thermal treatment device of claim 1, wherein said capacitor comprises a super capacitor.

4. The skin attachment type electric thermal treatment device of claim 3, wherein said super capacitor has a capacitance of 1 farad or more.

* * * * *